United States Patent
Casellas et al.

(10) Patent No.: US 6,767,533 B1
(45) Date of Patent: Jul. 27, 2004

(54) USE OF A SUBSTANCE BINDING WITH THE PERIPHERAL BENZODIAZEPIN RECEPTOR FOR TREATING SKIN STRESS

(75) Inventors: Pierre Casellas, Montpellier (FR); Jean-Marie Derocq, Murviel les Montpellier (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/831,720

(22) PCT Filed: Nov. 10, 1999

(86) PCT No.: PCT/FR99/02761

§ 371 (c)(1),
(2), (4) Date: May 14, 2001

(87) PCT Pub. No.: WO00/28947

PCT Pub. Date: May 25, 2000

(30) Foreign Application Priority Data

Nov. 17, 1998 (FR) .......................................... 98 14387

(51) Int. Cl.$^7$ ........................... A61K 7/42; A61K 31/74; C12P 1/00; C12N 1/20; A01N 63/02
(52) U.S. Cl. ................... 424/59; 424/78.02; 424/78.03; 424/401; 435/41; 435/119; 435/244; 435/251.1; 435/252.35; 435/253.2; 435/803; 435/886; 514/828; 514/947
(58) Field of Search ............................... 424/59, 78.02, 424/78.03, 401; 435/41, 119, 244, 251.1, 252.35, 253.2, 803, 886; 514/828, 947

(56) References Cited

U.S. PATENT DOCUMENTS

| | | | | |
|---|---|---|---|---|
| 4,011,140 A | * | 3/1977 | Komatsu | ..................... 435/119 |
| 5,614,178 A | * | 3/1997 | Bloom et al. | |
| 6,004,566 A | * | 12/1999 | Friedman et al. | ........... 424/400 |
| 2001/0016583 A1 | * | 8/2001 | Glick et al. | .................. 514/220 |

FOREIGN PATENT DOCUMENTS

JP         54073195 A   *   6/1979   ........... C12D/13/00

OTHER PUBLICATIONS

Levy, *A Psychosomatic Approach to the Management Of Recalcitrant Dermatoses*, 4(6), Nov. 1963, 334–337.
Ormfa et al., *Ricerche preliminari clinico–psicologiche su di un nuovo derivato benzodiazepinico (Nobrium) in dermatologia*, 45(5), May 1970, 325–339.
Carayon et al., *Involvement of Peripheral Benzodiazepine Receptors in the Protection of Hematopoietic Cells Against Oxygen Radical Damage*, 87(8), Apr. 1996, 3170–3178.
Boh et al., *Role of Reactive Oxygen Species in Dermatologic Diseases*, 14(4), Jul. 1996, 343–352.

* cited by examiner

*Primary Examiner*—Christopher R. Tate
*Assistant Examiner*—Kailash C. Srivastava
(74) *Attorney, Agent, or Firm*—Paul E. Dupont; Michael D. Alexander

(57) ABSTRACT

A composition containing a peripheral benzodiazepine receptor ligand for topical use in the treatment of cutaneous stress.

5 Claims, 7 Drawing Sheets

Figure 1:
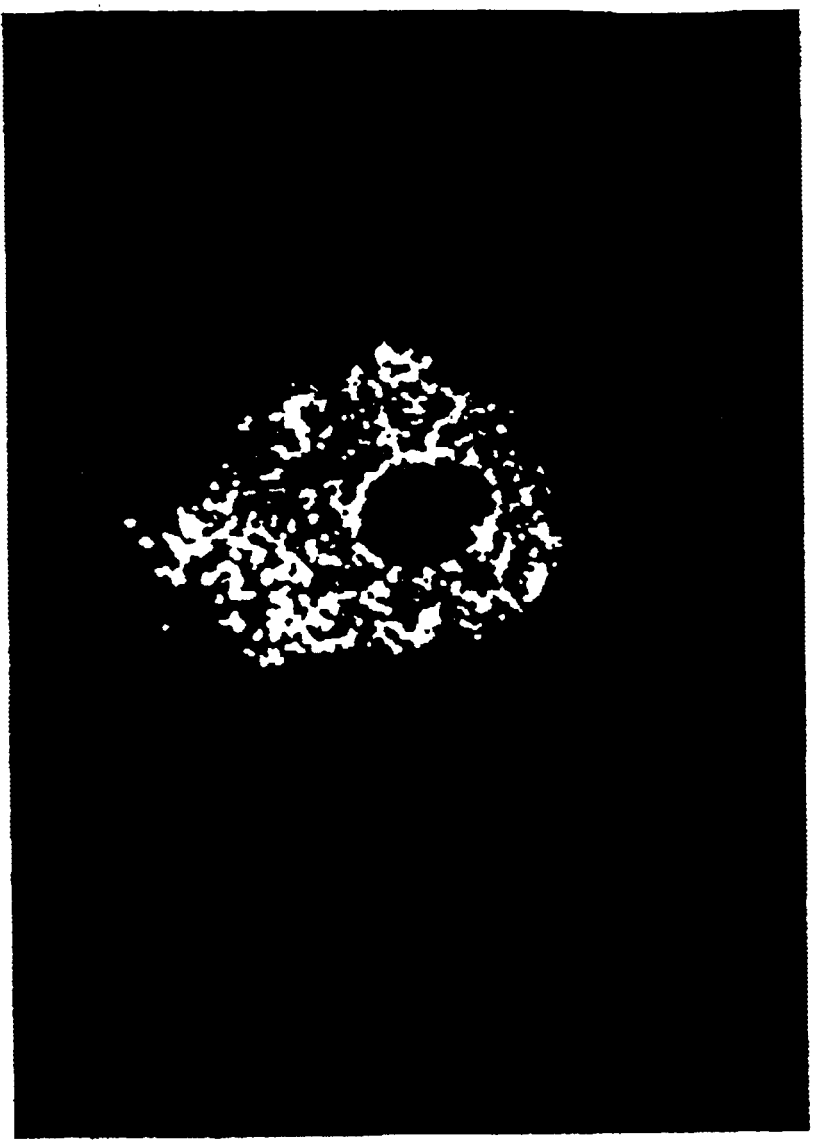

Analysis by confocal microscopy using the antibody 8D7 of the mitochondrial localization of the PBR receptor on keratinocytes A431 (green coloration).

The immunohistological analysis performed on a section of normal human epidermis reveals an expression of PBR which increases from the *stratum basale* to the *stratum corneum* (red coloration).

Expression of PBR on keratinocyte lines
and on normal human skin lines:

Western blot analysis

[kDa]   [SKIN]

8D7 antibody labeling (1 µg/ml final)

The deposits are normalized by assaying the total
proteins of the lysate;
deposits for each line 30 µg Curve of displacement of the reference ligand [3H]-PK11195 by Ro 5-4864 (peripheral ligand), clonazepam (central ligand) and diazepam (mixed ligand)

Involvement of PBR in the protection of hematopoietic cells against damage caused by oxygenated radicals

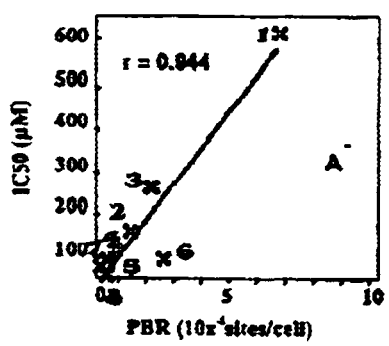

Correlation between the level of expression PBR [A] and of Bcl-2 [B] and of resistance to the toxicity of $H_2O_2$
1 = $THP_1$  2 = U937  3 = K562
IM9  5 = CEM  6 = NALM-6
7 = Jurkat  8 = RAJI

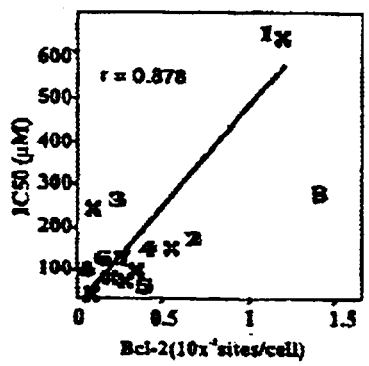

The $H_2O_2$ concentrations which induce 50% toxicity after incubation for 24 h [$IC_{50}$] are expressed as a function of the number of PBR or Bcl-2 sites.

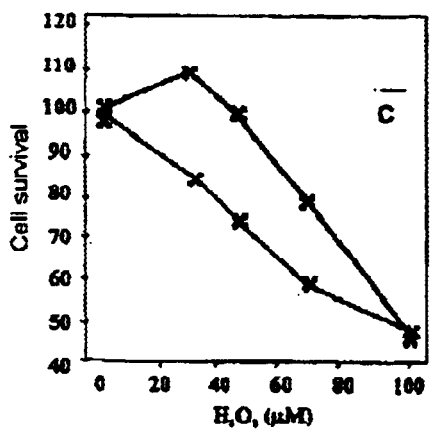

Viability of wild-type Jurkat cells ✕ and of cells transfected with PBR ✕ with respect to $H_2O_2$ toxicity after incubation for 24 h

FIGURE 6

Main ligands for the central and peripheral benzodiazepine receptors

USE OF A SUBSTANCE BINDING WITH THE PERIPHERAL BENZODIAZEPIN RECEPTOR FOR TREATING SKIN STRESS

The present invention relates to a composition for topical use containing a ligand for peripheral benzodiazepine receptors.

The invention relates to the use of a substance which binds specifically to the peripheral benzodiazepine receptor (PBR) for the manufacture of a composition for the prophylaxis or treatment of cutaneous stress.

The invention also relates to compositions containing these substances. These compositions may be cosmetic or pharmaceutical, and in particular topical dermatological compositions.

The term "cutaneous stress" means the various situations which may cause damage in particular to the epidermis, irrespective of the agent causing this damage. This agent may be inside and/or outside the body, for instance a chemical or free-radical agent or alternatively an external agent such as ultraviolet radiation.

The composition according to the invention is thus intended to prevent and combat skin irritation, dry patches, erythema, dysesthetic sensations, sensations of heating, pruritus of the skin and/or mucous membranes, and ageing, and may also be used in skin disorders such as, for example, psoriasis, pruriginous diseases, herpes, photodermatitis, atopic dermatitis, contact dermatitis, lichens, prurigo, pruritus, insect bites, in fibrosis and other disorders of collagen maturation, in immunological disorders or in dermatological conditions such as eczema.

The PBR ligand, also referred to as "substance", contained in the composition may be a non-peptide compound, a peptide, a cell extract or tissue extract of animal or plant origin or a product obtained by fermenting a microorganism, for example fermenting a bacterium or fungus.

Figure 7:
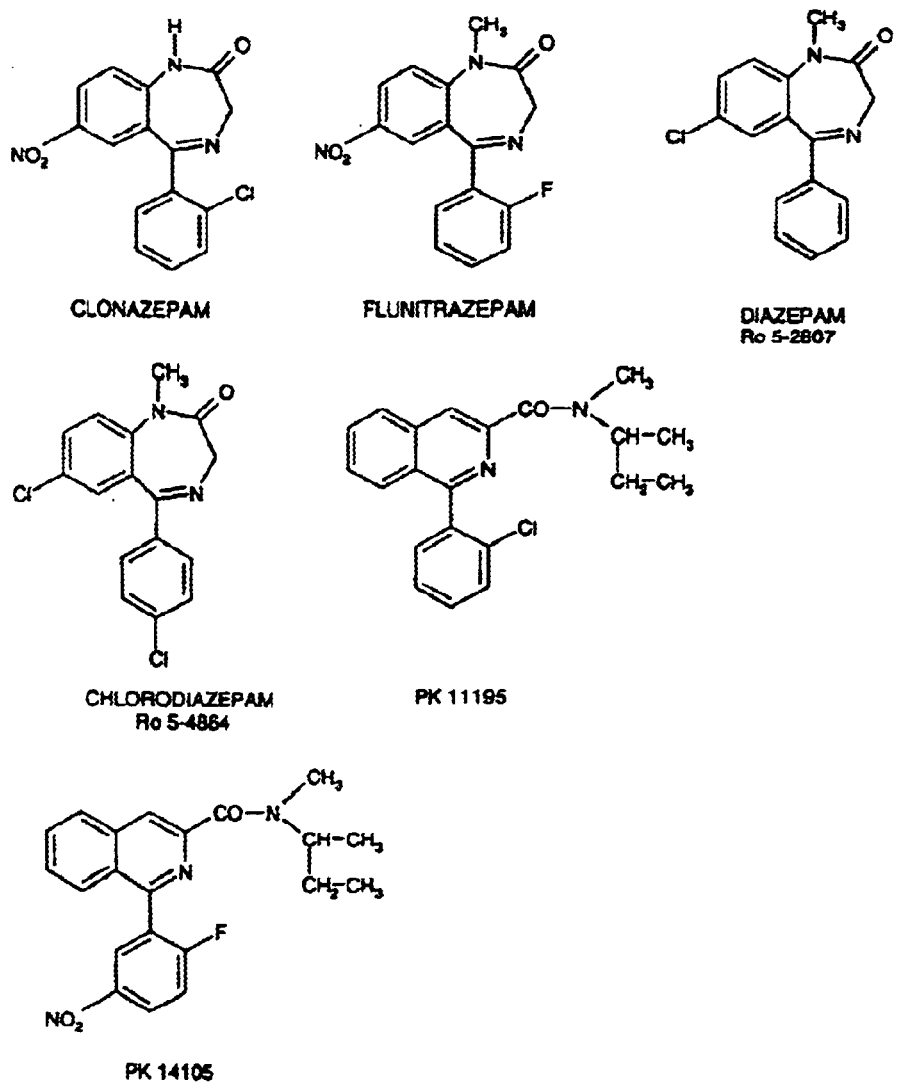

Many PBR ligands are disclosed in the literature (FIG. 7). Examples which may be mentioned include Ro 5-4864 or chlorodiazepam, Ro 5-2807 or diazepam and PK 11195, or reference may be made to the article Peripheral Benzodiazepine Receptors, Ch. III, J. J. Bourguignon, Ed. E. Giesen—Crouse, Academic Press.

PBR is an 18-kd protein located on the outer membrane of the mitochondria of peripheral tissues. It consists of five transmembrane domains and of a carboxy-terminal portion directed towards the cytosol. Several functions are attributed to PBR depending on the nature of the tissue under consideration: regulation of steroidogenesis, biosynthesis of heme, cell differentiation and growth, control of mitochondrial respiration (Krueger K E, Biochimica and Biophysica Acta 1995, 1241, 453–470). Although its precise function has not yet been fully elucidated, several recent experimental data suggest that PBR might play a fundamental role in regulating the processes of programmed cell death and in protection against free radicals.

It has been shown that PBR is in fact closely associated at the mitochondrial level with apoptosis regulatory proteins such as Bcl2 which prevents rupture of the mitochondrial membrane potential, thus preventing the apoptosis induced in particular by the production of reactive oxygenated radicals (Marchetti P. et al., J. Exp. Med. 1996, 184, 1155–1160); (Marchetti P. et al., J. Immunol. 1996, 157, 4830–4836).

In the context of the present invention, the protective role of PBR against free radicals was directly observed on cells of hematopoietic origin for which a close correlation between the PBR density and the protection against free radicals was demonstrated. Furthermore, in this same study, it was demonstrated that the transfection of PBR into cells lacking this receptor gives protection against the damage caused by oxygenated species (Carayon P. et al., Blood 1996, 87, 3170–3178).

Several literature data suggest that PBR might play an important role in regulating apoptosis processes and in protecting cells against damage caused by free radicals.

Recent phylogenic studies reinforce this novel notion that PBR acts as an apoptosis modulator involved in antioxidant functions. The reason for this is that significant similarities exist between PBR and the protein CrtK of *Rhodobacter sphaeroides*, a photo-synthetic bacterium. This bacterial protein which functions as a photosensitive oxygen detector, regulates the expression of the genes involved in photosynthesis in response to environmental changes in oxygen tension and in light intensity. The comparison between PBR and CrtK reveals 35% identity and a conservation of sequence between these two proteins which diverged in the phylogeny two billions years ago. This homology suggests a highly specialized and conserved function of PBR which appears to be similar to that of CrtK in the bacterium. Specifically, it has recently been demonstrated that mammalian PBR transfected into Rhodobacter CrtK mutants complements the oxygen-detecting function of CrTK. Thus, this study suggests a key role of PBR in the transduction of oxygen-dependant signals (Yeliseev A A., et al., Proc. Natl. Acad. Sci. 1997, 94, 5101–5106).

However, to date, no substance has ever been precisely indicated as a specific ligand for cutaneous PBR receptors, which is all the more reason why no topically active substance which binds specifically to the PBR receptors has ever been disclosed in the literature.

Figure 2:
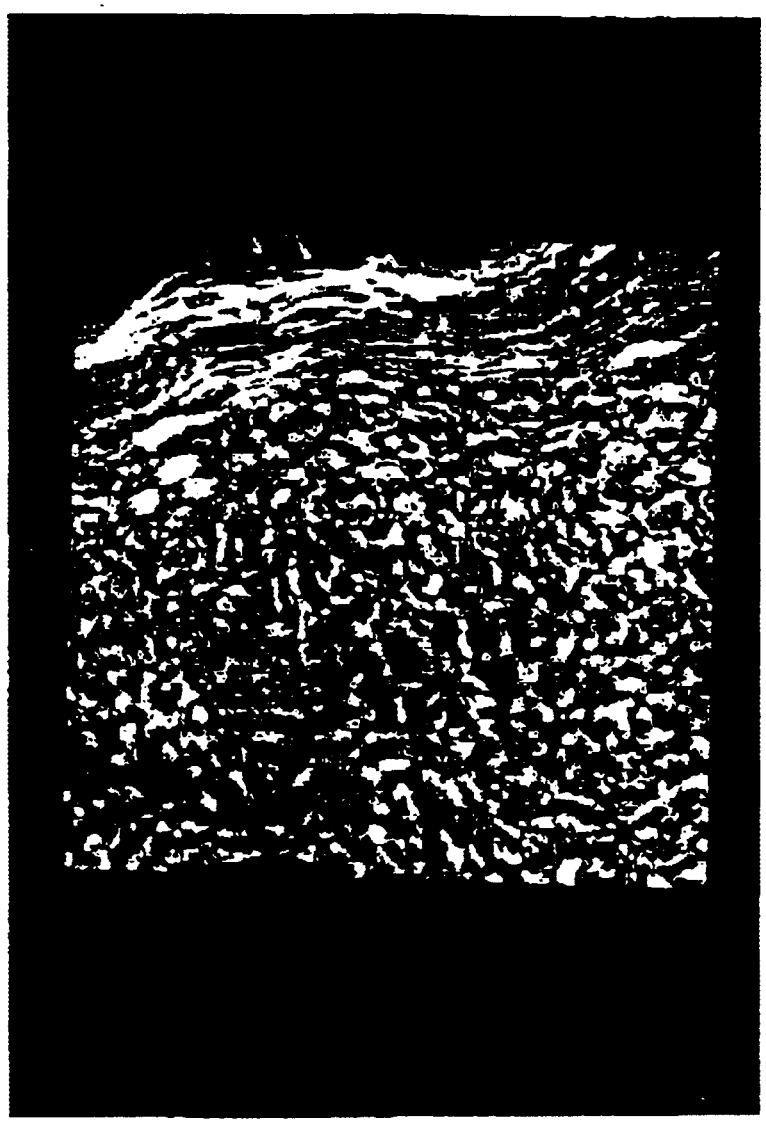

It has now been shown, in the context of the present invention, that PBR is abundantly expressed in the skin within the various cell compartments of which it is composed: keratinocytes, Langerhans cells, hair follicles and endothelial cells of the dermal vascular system. In the skin, the expression of PBR follows an increasing gradient from the basal layer to the horny layer. This noteworthy organization which favors the differentiated cells of the epidermis that are the most exposed to external stresses is undoubtedly of a primordial physiological importance for protecting the most vulnerable areas of the epidermis. Subcellular studies performed by confocal microscopy indicate, as expected, a colocalization of PBR with Bcl2 in the mitochondrian. Histological studies on skin sections have revealed a surprising distribution of PBR (FIGS. 1 and 2).

Specifically, the expression of this receptor in the epidermis follows a gradient of increasing density from the basal layers to the most differentiated layers of keratinocytes. This highly organized spatial distribution which favors, in terms of density, the outermost and thus the most exposed cells of the epidermis, leads to the assumption that PBR in the skin might represent a natural protection system against free radicals generated by exposure to ultraviolet radiation. The concomitant observation that the distribution of the anti-apoptotic protein Bcl2 obeys a strictly inverse gradient suggests a compensatory role of PBR in preserving the cells that are most differentiated.

This set of data which suggest a protective function of PBR, more particularly in the epidermis, has led to the discovery of natural or synthetic ligands, showing that their interaction with PBR could be beneficial in various situations of cutaneous stress induced by chemical or free-radical agents or alternatively following an exposure to UV.

Thus, according to one of its aspects, the present invention relates to the use of a ligand which is specific for PBR, Ro 5-4864, in cutaneous stress. This ligand is a PBR agonist.

According to another aspect of the invention and on the basis of these observations, a screening directed toward finding natural PBR ligands was undertaken and made it possible to isolate several fractions capable of interacting with this receptor. The potentially protective effect of these natural ligands was then evaluated in various tests inducing a cutaneous stress and in particular in tests of cutaneous erythema induced by UV irradiation. Radical-scavenging properties and skin repair capacities were also investigated.

Biochemical and pharmacological tests were used to demonstrate the activity and advantage of the substances in various situations of cutaneous stress.

The tests performed with PBR were aimed at showing its potential involvement in regulating apoptotic processes and in preserving skin cells against various deleterious stress situations.

EXAMPLE 1

Immunohistological Studies of Cutaneous Localization of PBR

A Western blot analysis made it possible to demonstrate the abundant presence of PBR on six different lines of human keratinocytes and on normal human skin (FIG. 1), using specific anti-PBR antibodies Ac 8D7 (anti-PBR mouse mAb, isotype IgG1, Dussossoy et al., Cytometry, 1996, 24:39–48). At the subcellular level, the analyses performed by confocal microscopy confirm a colocalization of PBR at the mitochondrial level in keratinocytes (FIG. 2).

Figure 3:
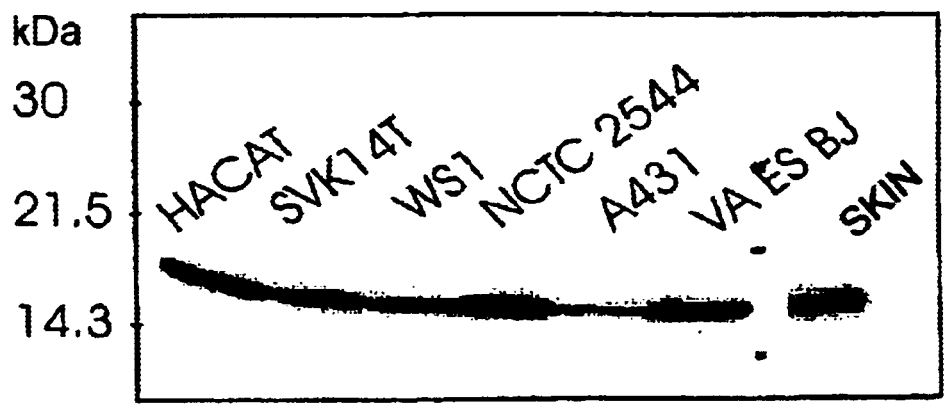

An immunohistological study performed on a normal human epidermal section using the same antibody reveals a very particular organization since the expression of PBR increases from the stratum basale to the stratum corneum. This receptor is thus abundantly present on the keratinocytes that are most differentiated, located directly under the stratum corneum (FIG. 3).

EXAMPLE 2

Binding and Specificity Studies

Figure 4:
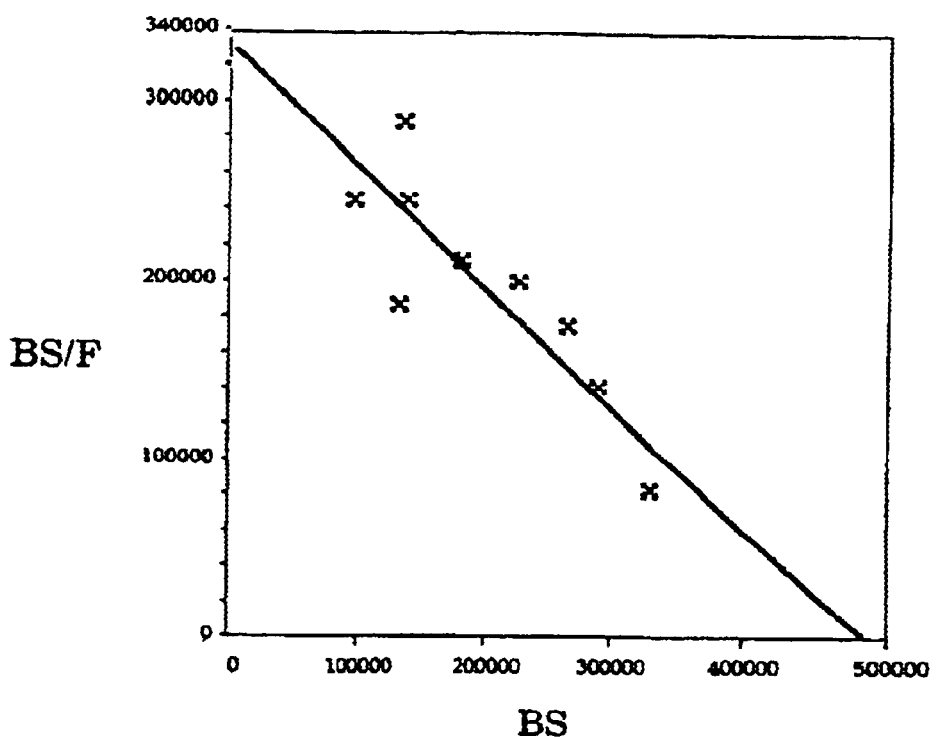
Figure 5:
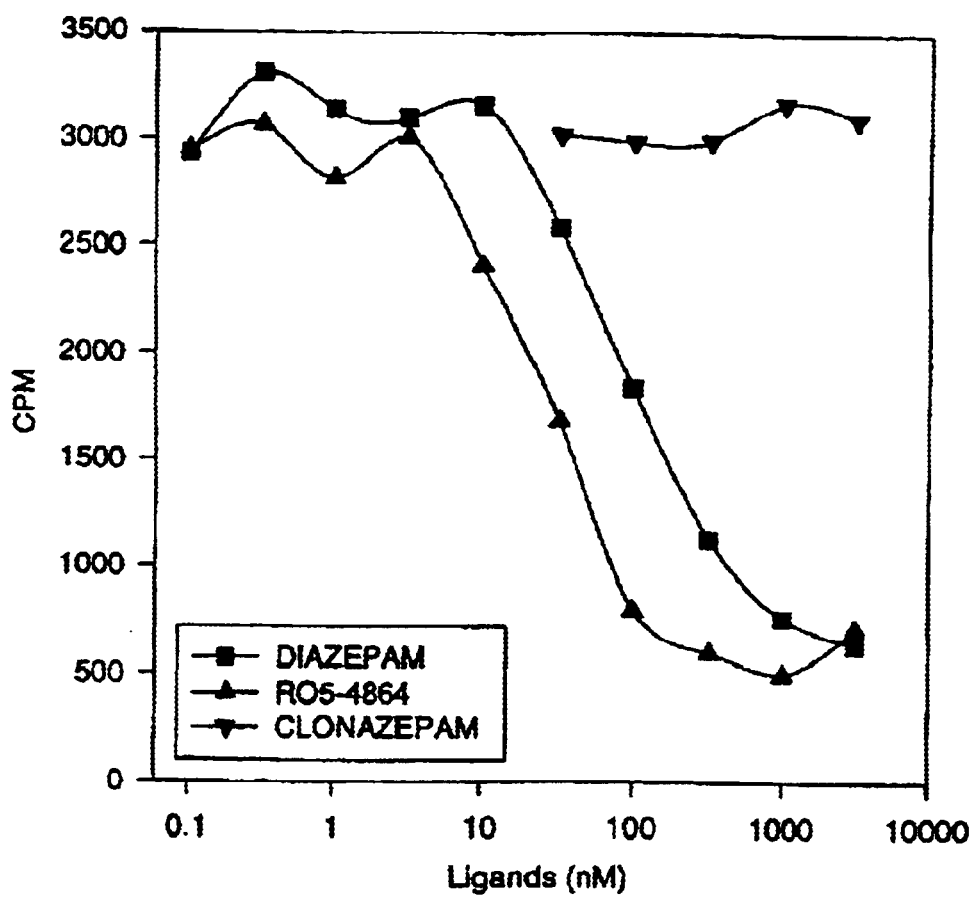

The binding studies were performed on the keratinocyte line A-431 (human epidermoid carcinoma (ATCC, CRL-1555)) by displacement of the reference ligand [$^3$H]-PK11195. Scatchard analysis indicates a single binding site, a density of about 470 000 receptors per cell and high affinity of the ligand (KD=1.5 nM) (FIG. 4). The specificity of the binding to the peripheral receptor borne by the keratinocytes is confirmed by the pharmacological studies which show a decreasing efficacy of the displacement of the reference peripheral ligand (PK 11195) by the following ligands: Ro 5-4864=(IC$_{50}$≈25 nM)>diazepam (IC$_{50}$≈100 nM)>>>clonazepam (inactive at 3 200 nM). It is recalled that this last compound is a ligand of the central receptor for benzodiazepines, diazepam is mixed and Ro 5-4864 is specific for PBR (FIG. 5).

EXAMPLE 3

Involvement of PBR in Protection Against Oxygenated Radicals

Two types of experiment are described in FIG. 6. The first consists in comparing different lines of lymphoid or myeloid origin as regards their ability to withstand the toxicity of oxygenated radicals in relation with their level of expression of PBR. The results indicate a very strong correlation between the number of PBR sites per cell and the resistance to the toxicity induced by $H_2O_2$. There is also a similar correlation when, this time, the level of expression of Bcl2, a protein known to protect cells against oxidative damage, is considered. These data, combined with the fact that Bcl2 and PBR are proteins located on the outer mitochondrial membrane, suggest that they may have common functions in cell protection. Interestingly, although the expression of PBR follows a density gradient which increases from the basal layer to the limit of the horny layer, the literature data indicate an inverse phenomenon for the expression of Bcl2, suggesting that during the differentiation of keratinocytes, PBR may take over from Bcl2 as regards the functions of protection against free radicals.

In the second experiment, the possible role of PBR in protection against the toxicity of free radicals is reinforced by the demonstration of the better viability, in the presence of $H_2O_2$, of PBR+transfected Jurkat cells in comparison with homologous PBR-cells.

EXAMPLE 4

The anti-apoptotic activity of the active agents was measured on human keratinocytes and on fibroblasts (ATCC) which were inoculated in 35 mm Petri dishes (5×10$^5$ cells/well) in DMEM (Dubelco's Mode Eagle Medium) supplemented with 10% fetal calf serum and left to proliferate to the point of confluence. This culture medium is then drawn off, the cells are rinsed and 0.1% fetal calf serum is added in the presence of a saline solution. Increasing concentrations of the substance to be studied are added. Twenty four hours later, the apoptosis is measured with an ELISA (enzyme-linked immunosorbent assay) assay kit.

Keratinocytes were subjected to ultraviolet radiation of type B (UVB) at a dose of 250 J/m$^2$ for 16 hours (J. Invest. Dermatol. 1995, 104: 922–927). In the presence of the PBR ligand Ro 5-4864, it was shown that the cell impairment processes induced by the irradiation are prevented in a ligand concentration range of between 10 nM and 10 μm.

EXAMPLE 5

The photoprotective effect of the ligand was evaluated by cutaneous application to albino guinea pigs.

The cutaneous topical route is used in order to reproduce the conditions of utilization in man.

Harley-guinea pigs, from Charles River France, Saint Aubin les Elbeuf, 76410 Cléon, France, are used.

The animals were shaved and the hair on the right and left hind flanks was then plucked 24 hours before the start of the treatment.

The animals were irradiated immediately before the first treatment. The energy is checked before each irradiation performed on the right and left flanks, in the UVB spectrum at a dose of 4 000 mJ/cm$^2$.

The right flank of the animals was treated with 0.2 ml of ligand solution immediately after irradiation and then 2 and 5 hours after irradiation. The left flank will not be treated.

A Xeron high pressure vapor lamp (IDEM 300) will produce the irradiation.

The local reactions are read before treatment and then 5 and 24 hours after irradiation. Erythema and edema were evaluated as follows:

Erythema 0 no erythema; 1 very mild, barely perceptible erythema; 2 distinct, pale pink erythema; 3 distinct, bright red erythema; 4 particularly intense erythema Edema 0 no edema; 1 very mild edema (barely visible); 2 mild edema (contours well defined and swelling apparent); 3 moderate edema (thickness of about 1 mm); 4 serious edema (thickness greater than 1 mm and area greater than the area of application).

Examples of natural ligands for the PBR receptor which are produced by fermentation are described below with their activity.

A screening carried out on microorganism extracts performed on solid or liquid medium made it possible to select three strains of microorganisms (microscopic fungi and bacteria).

The three strains selected after various studies performed to optimize the conditions for producing significant amounts of culture extracts having good activities in the test for measuring the interaction with the PBR receptor, have the references SRL 4988, SRL 5186 and SRL 5189.

The above three strains were filed at the CNCM of the Institut Pasteur: date of 27 Aug. 1999 with the respective serial numbers I-2305, I-2306 and I-2307.

The strain SRL 4988 classified as Nocardia species, isolated from a soil sample, has the following ecologico-physiological properties, determined after culturing for two weeks at 28° C. on ISP2 medium: negative phototroph, chemo-organotroph, mesophile and negative halophile. It is immobile and has open, non-verticillate whorls.

The strain SRL 5186 classified as Streptomyces species, isolated from a soil sample, has the following ecologico-physiological properties, determined after culturing for two weeks at 28° C. on ISP2 medium: negative phototroph, chemo-organotroph, mesophile and negative halophile. It is immobile and has flexible, biverticillate hyphae.

The strain SRL 5189 classified as Actinosinnema species has the following ecologico-physiological properties, determined after culturing for two weeks at 28° C. on ISP2 medium: negative phototroph, chemo-organotroph, mesophile, negative halophile. It is immobile and has flexible, monoverticillar hyphae.

These strains, and also their productive mutants, thus constitute a further subject of the invention.

After culturing on nutrient agar medium and several successive subculturings which produce an abundant and pure culture, a storage batch 0 of the stock strain and then primary and secondary inoculation batches are prepared.

To do this, a spore suspension is prepared from a culture on nutrient agar medium in a Petri dish and from an uptake medium; this medium contains a cryoprotective agent to ensure good viability of the spores during the storage by freezing.

The spore suspension obtained is distributed into cryotubes which will be stored at −80° C.: these tubes constitute batch 0.

By following the same protocol, but using a tube from batch 0, a primary inoculation batch is prepared. Next, again according to the same protocol, a secondary inoculation batch is prepared from a primary inoculation cryotube. Manufacture of the inoculation batches 0, 1 and 2 ensures long-lasting availability of the strain and thus of the desired activity. The culturing of these three strains for obtaining natural ligands of the PBR receptor may be carried out in a similar manner with the usual aerobic culture means, i.e. liquid media in fermenters of any volume with in-line monitoring of the pH and the aeration.

EXAMPLE A SRL 4988

As an example of culturing in conical flasks for the strain SRL 4988: a secondary inoculation tube is used to inoculate Petri dishes prepared with a medium for promoting actinomycetes sporulation according to the composition:

| | |
|---|---|
| Glucose | 20 g |
| Soyoptim (SIO) | 10 g |
| $CaCO_3$ (OMYA) | 3 g |
| Agar type E | 20 g |
| Distilled water qs | 1 l |

The cultures are incubated in dishes for 5 days at 28° C. A spore suspension is then obtained by adding 10 ml of a liquid medium of the composition below to each Petri dish:

| | |
|---|---|
| Glucose | 30 g |
| Soyoptim (SIO) | 10 g |
| Tryptone U.S.P. (Biokar) | 4 g |
| Yeast extract (Difco) | 8 g |
| NaCl | 2.5 g |
| $CaCO_3$ | 5 g |
| Casein hydrolyzate | 5 g |
| Soybean papain peptone | 5 g | the pH of which is adjusted to 7.0 before sterilization.

5 ml of the spore suspensions are used to inoculate sterile 250 ml flasks, containing 50 ml of the same medium, which constitute the precultures, incubated in a warm chamber at 28° C. on a shaker with shelves, or in an autonomous incubator, the rotation speeds in either of the systems being set at 210 rpm.

After shaking for two days, the preculture flasks are used to inoculate the actual culture flasks at a rate of 5 ml of preculture medium per 500 ml conical flask containing culture medium (100 ml) having the composition:

| | |
|---|---|
| Glycerol | 10 g |
| Soluble starch | 30 g |
| Soyoptim | 15 g |
| Tryptone | 2 g |
| Yeast extract | 5 g |
| $CaCO_3$ | 5 g |
| Trace element solution | 10 ml |
| Water qs | 1 l |
| pH7 | |

Composition of the trace element solution used:

| | |
|---|---|
| $FeSO_4 \cdot 7 H_2O$ | 1.0 g |
| $MnSO_4 \cdot 4 H_2O$ | 1.0 g |
| $CaCl_2 \cdot 2 H_2O$ | 0.025 g |
| $CaCl_2 \cdot 2 H_2O$ | 0.10 g |
| $H_3BO_3$ | 0.56 g |
| $(NH_4)_6Mo_7O_{24} \cdot 4 H_2O$ | 0.002 g |
| $ZnSO_4 \cdot 7 H_2O$ | 0.20 g |
| Water qs | 1 l |

Thus, in this specific case, five preculture flasks were used to inoculate 40 culture flasks with 100 ml of culture medium per 500 ml conical flask, which, after shaken culturing for 6 days at 28° C. in a warm chamber on a rotary shaker set at 210 rpm, give 4 liters of bacterial suspension.

The 4 liters of fermentation broth are centrifuged several times, at a temperature of 4° C. and under a regime of 13 500 rpm (i.e. 27 500×g with the rotor used), in order to separate out the biomass, i.e. the pellet combining the cells from the culture supernatant consisting mainly of water from the nutrient medium used and containing in solution residues of components of the nutrient medium and also metabolites produced and excreted by the bacterial cells during the various phases of their growth.

The biomasses and supernatants are then frozen at −20° C.

EXTRACTION OF THE NATURAL LIGANDS OF THE PBR RECEPTOR

The 4 liters of thawed supernatant are placed in a 10 liter beaker. 400 g of Amberlite XAD 16 poly-styrene-divinylbenzene resin (Rohm & Haas) are added to the solution. The suspension is shaken using a motor equipped with a paddle shaft, rotating at 20 rpm, for 15 hours. The solution is then filtered, the filtrate is removed and the drained resin is taken up in 1 liter of methanol. This mixture is stirred gently for 1 hour. The resin is again filtered off and retreated in an identical manner with 1 liter of methanol. During a third operation, the resin is retreated, this time with 1 liter of acetone. The drained resin is then removed and the 3 liters of combined organic solvent are evaporated to dryness in a rotary evaporator under vacuum.

The evaporation residue (17.7 g) is slurried in 50 ml of methanol, the suspension obtained is centrifuged at 3 000 rpm for 15 minutes and the settled supernatant obtained constitutes the culture supernatant extract.

This extract is tested in dilution for inhibition of the binding to the PBR receptor, and gives an activity evaluated at 1/200 (50% inhibition).

The combined biomasses (199 g) in a 2 liter beaker are treated, with stirring, with a mixture of 750 ml of methylene chloride and 750 ml of methanol. Stirring is continued for 15 hours at room temperature. The suspension is then filtered and the clear solution obtained is concentrated under vacuum in a rotary evaporator. The evaporation residue (5.4 g) is then slurried in 50 ml of methanol and constitutes the biomass extract.

This extract is tested for inhibition of the binding of the PBR receptor, and gives an activity measured at 1/2200 (ID 50=2200$^{-1}$).

EXAMPLE B SRL 5186

With the same respective protocols and media:
agar medium for the subculturings on Petri dishes
liquid preculture medium
liquid production medium,
14×500 ml conical flasks containing 100 ml of production medium, and inoculated to 5%, are incubated at 28° C. in a warm chamber on a rotary shaker rotating at 210 rpm, for 6 days.

After centrifugation and storage of the production supernants and biomasses for one to two days in a freezer at −20° C., these products are thawed before proceeding with their extraction.

The biomasses (54.9 g) are treated in a beaker, with stirring, with a mixture of 250 ml of dichloromethane and 250 ml of methanol, for ten hours. The suspension is then filtered and the clear solution obtained is concentrated to dryness on a rotary evaporator.

The dry residue (1.4 g) is slurried in 17.5 ml of methanol and the suspension obtained is centrifuged at 3 000 rpm for 15 minutes. The centrifugation supernatant collected constitutes the biomass extract.

This extract, evaluated in dilution on the test for inhibition of binding to the PBR receptor, gives a 50% inhibition in the test at a dilution of 1/3750 (ID$_{50}$=3 750$^{-1}$).

160 g of XAD 16 polystyrene-divinylbenzene resin (Rohm & Haas) are added to the 1 400 ml of thawed supernatant and the suspension is stirred for 15 hours. The resin is filtered off, the filtrate is removed and the resin is retreated with 200 ml of solution containing 25% methanol in water for 3 hours.

The resin is filtered off and this second filtrate is removed. The resin then undergoes three similar treatments, two with 200 ml of methanol and the last with 200 ml of acetone. These last three filtrates are combined in a round-bottomed flask and then concentrated under vacuum on a rotary evaporator. The dry residue obtained (2.2 g) is then slurried in 17.5 ml of methanol and the solution obtained constitutes the supernatant extract.

This extract, evaluated in dilution on the test for inhibition of the binding to the PBR receptor, gives a 50% inhibition at a dilution of 1/940 (ID$_{50}$=940$^{-1}$).

EXAMPLE C SRL 5189

With the same respective protocols and media:
agar medium for the subculturings on Petri dishes
liquid preculture medium
liquid production medium,
10×500 ml conical flasks containing 100 ml of production medium, inoculated to 5%, are incubated at 28° C. in a warm chamber on a rotary shaker rotating at 210 rpm, for 8 days.

After centrifugation and storage of the production supernants and biomasses for one to two days in a freezer at −20° C., these products are thawed before proceeding with their extraction.

The biomasses (69.5 g) are treated in a beaker, with stirring, with a mixture of 150 ml of dichloromethane and 150 ml of methanol, for ten hours. The suspension is then filtered and the clear solution obtained is concentrated to dryness on a rotary evaporator. The dry residue (1.5 g) is slurried in 12.5 ml of methanol and the solution obtained is centrifuged at 3 000 rpm for 15 minutes. The centrifugation supernatant collected constitutes the biomass extract. This extract, evaluated in dilution on the test for inhibition of the binding to the PBR receptor, gives a 50% inhibition in the test at a dilution of 1/2600 (ID$_{50}$=2 600$^{-1}$).

100 g of XAD 16 polystyrene-divinylbenzene resin (Rohm & Haas) are added to the 1 000 ml of thawed supernatant and the suspension is stirred for 15 hours. The resin is filtered off, the filtrate is removed and the resin is retreated with 150 ml of a solution containing 25% methanol in water, for 3 hours. The resin is filtered off and this second filtrate is removed. The resin then undergoes three similar treatments, two with 150 ml of methanol and the last with 150 ml of acetone. These last three filtrates are combined in a round-bottomed flask and then concentrated under vacuum on a rotary evaporator. The dry residue obtained (1.7 g) is then slurried in 12.5 ml of methanol and the solution obtained constitutes the supernatant extract.

This extract, evaluated in dilution on the test for inhibition of the binding to the PBR receptor, gives a 50% inhibition at a dilution of 1/600 (ID$_{50}$=500$^{-1}$).

In the compositions according to the invention, the substance which binds to PBR is preferably used in an amount ranging from 0.00001 to 20% by weight relative to the total weight of the composition and in particular in an amount ranging from 0.001% to 10% by weight relative to the total weight of the composition.

The compositions according to the invention may be in any presentation form normally used for topical application.

The amounts of the various constituents in the compositions according to the invention are those conventionally used in the fields under consideration and are appropriate for their presentation form.

For a topical application, the compositions of the invention comprise a medium which is compatible with the skin. These compositions may especially be in the form of aqueous, alcoholic or aqueous-alcoholic solutions, gels, water-in-oil or oil-in-water emulsions having the appearance of a cream or a gel, micro-emulsions or aerosols, or alternatively in the form of vesicular dispersions containing ionic and/or nonionic lipids. These presentation forms are prepared according to the usual methods of the fields under consideration.

These compositions for topical application may in particular constitute a cosmetic or dermatological protective, treatment or care composition for the face, for the neck, for the hands or for the body (for example day creams, night creams, antisun creams or oils or body milks), a make-up composition (for example a foundation) or an artificial tanning composition.

When the composition of the invention is an emulsion, the proportion of fatty substances it contains may range from 5% to 80% by weight and preferably from 5% to 50% by weight relative to the total weight of the composition. The fatty substances and emulsifiers used in the composition in emulsion form are chosen from those conventionally used in cosmetics or dermatology.

As fatty substances which may be used in the invention, mention may be made of mineral oils (petroleum jelly), plant oils (liquid fraction of karite butter) and hydrogenated derivatives thereof, animal oils, synthetic oils (perhydrosqualene), silicone oils (polydimethylsiloxane) and fluoro oils. Other fatty substances which may also be mentioned included fatty alcohols (cetyl alcohol or stearyl alcohol), fatty acids (stearic acid) and waxes.

The emulsifiers may be present in the composition in a proportion ranging from 0.3% to 30% by weight and preferably from 0.5% to 30% by weight relative to the total weight of the composition.

In a known manner, the cosmetic or dermatological compositions of the invention may also contain adjuvants that are common in the corresponding fields, such as hydrophilic or lipophilic gelling agents, preserving agents, antioxidants, solvents, fragrances, fillers, screening agents and dyestuffs. Moreover, these compositions may contain hydrophilic or lipophilic active agents. The amounts of these various adjuvants or active agents are those conventionally used in cosmetics or dermatology, and, for example, from 0.01% to 20% of the total weight of the composition. Depending on their nature, these adjuvants or these active agents may be introduced into the fatty phase, into the aqueous phase and/or into the lipid vesicles.

Among the active agents which the compositions of the invention may contain, mention may be made in particular of active agents which have an effect on treating wrinkles or fine lines, and in particular keratolytic active agents. The term "keratolytic" means an active agent which has desquamating, exfoliant or scrubbing properties, or an active agent capable of softening the horny layer.

Among these active agents with an effect on treating wrinkles and fine lines, which the compositions of the invention may contain, mention may be made in particular of hydroxy acids and retinoids.

The hydroxy acids may be, for example, α-hydroxy acids or β-hydroxy acids, which may be linear, branched or cyclic, and saturated or unsaturated. The hydrogen atoms of the carbon chain may also be substituted with halogens, halogenated, alkyl, acyl, acyloxy, alkoxycarbonyl or alkoxy radicals containing from 2 to 18 carbon atoms.

The hydroxy acids which may be used are, in particular, glycolic acid, lactic acid, malic acid, tartaric acid, citric acid, 2-hydroxyalkanoic acid, mandelic acid, salicylic acid and the alkyl derivatives thereof, for instance 5-n-octanoylsalicylic acid, 5-n-dodecanoylsalicylic acid, 5-n-decanoylsalicylic acid, 5-n-octylsalicylic acid, 5-n-heptyloxysalicylic acid or 4-n-heptyloxysalicylic acid, and 2-hydroxy-3-methylbenzoic acid or alkoxylated derivatives thereof, for instance 2-hydroxy-3-methoxybenzoic acid.

The retinoids may be in particular retinoic acid and derivatives thereof, retinol (vitamin A) and esters thereof such as retinyl palmitate, retinyl acetate or retinyl propionate, and salts thereof.

These active agents may be used in particular in concentrations ranging from 0.0001% to 5% by weight relative to the total weight of the composition.

What is claimed is:

1. A topical composition for treating cutaneous stress containing as active principle a substance that binds to the peripheral benzodiazepine receptor, wherein said substance is a fermentation product of Nocardia SRL 4988, Streptomyces SRL 5186 or Actinosinnema SRL 5189 present in an amount of from 0.00001% to 20% by weight relative to the total weight of the composition.

2. A composition according to claim 1 wherein the substance that binds to the peripheral benzodiazepine receptor is present in an amount of from 0.001% to 10% by weight relative to the total weight of the composition.

3. A method for the treatment of cutaneous stress which comprises topically administering to a subject in need of such treatment an effective amount of a composition according to claim 1.

4. A method for the treatment of cutaneous stress which comprises topically administering to a subject in need of such treatment an effective amount of a composition according to claim 1.

5. A method for reducing wrinkles, reducing solar erythema or protecting against free radicals which comprises topically administering an effective amount of a composition according to claim 1.

* * * * *

UNITED STATES PATENT AND TRADEMARK OFFICE
CERTIFICATE OF CORRECTION

PATENT NO. : 6,767,533 B1 Page 1 of 1
DATED : July 27, 2004
INVENTOR(S) : Casellas Pierre et al.

It is certified that error appears in the above-identified patent and that said Letters Patent is hereby corrected as shown below:

<u>Column 10,</u>
Lines 48-49, "a composition according to claim 1." should read -- a composition according to claim 2. --.

Signed and Sealed this

Twenty-first Day of March, 2006

JON W. DUDAS
*Director of the United States Patent and Trademark Office*